United States Patent [19]
Takegawa et al.

[11] Patent Number: 5,985,637
[45] Date of Patent: Nov. 16, 1999

[54] GENE ENCODING ENDO-β-N-ACETYLGLUCOSAMINIDASE A

[75] Inventors: Kaoru Takegawa; Shojiro Iwahara, both of Kagawa-ken, Japan

[73] Assignee: Takara Shuzo Co., Ltd., Kyoto-fu, Japan

[21] Appl. No.: 08/969,714

[22] Filed: Nov. 19, 1997

Related U.S. Application Data

[63] Continuation of application No. 08/736,607, Oct. 25, 1996, abandoned.

[30]     Foreign Application Priority Data

Oct. 27, 1995  [JP]  Japan .................................. 7-303864

[51] Int. Cl.$^6$ .............................. C12N 9/24; C12N 15/00; C12P 21/06; C07H 21/04
[52] U.S. Cl. ..................... 435/200; 435/69.1; 435/252.3; 435/320.1; 536/23.2; 536/23.7; 530/350
[58] Field of Search ..................... 435/200, 201, 435/205, 69.1, 252.3, 320.1, 830; 530/350; 536/23.2, 23.7

[56]        References Cited

FOREIGN PATENT DOCUMENTS

539160A1   4/1993   European Pat. Off. .
5064594    3/1993   Japan .

OTHER PUBLICATIONS

Takegawa et al. (1995). J. Biol. Chem. 270(7), 3094–9, Feb. 17, 1995.
Takegawa et al. (1989). Appl. Environ. Microbiol. (1989). 55,3107–12. [cited in Takegawa et al. (1995) and in Applicants' disclosure, describes the purified protein.], 1989.
Takegawa et al. (1989) Applied and Environmental Microbiology, vol. 55, No. 12, pp. 3107–3112.
Kaoru Takegawa et al., "Cloning, Sequencing, and Expression of . . . ", Archives of Biochemistry and Biophysics, vol. 338, No. 1, Feb. 1, 1997, pp. 22–28.
Kaoru Takegawa et al., "Induction and Purification of . . . ", Applied And Environmental Microbiology, Dec. 1989, vol. 55, No. 12, pp. 3107–3112.
Abstract, C.H. Martin et al., "Sequencing of the alcohol dehydrogenase (ADH) region of Drosophila melonogaster", Sep. 21, 1994, Database EMBL, Accession No. L36278.

*Primary Examiner*—Robert A. Wax
*Assistant Examiner*—Tekchand Saidha
*Attorney, Agent, or Firm*—Birch, Stewart, Kolasch and Birch, LLP

[57]         ABSTRACT

An isolated DNA having a sequence encoding a polypeptide possessing endo-β-N-acetylglucosaminidase A activity or functionally equivalent variants thereof; and a method for producing a polypeptide possessing endo-β-N-acetylglucosaminidase A activity or functionally equivalent variants thereof using the isolated DNA by recombinant DNA technology.

8 Claims, 3 Drawing Sheets

GENE ENCODING ENDO-β-N-ACETYLGLUCOSAMINIDASE A

This application is a continuation of application Ser. No. 08/736,607 filed on Oct. 25, 1996, now abandoned.

BACKGROUND OF THE INVENTION

1. Field of the Invention

The present invention relates to a DNA encoding a polypeptide possessing endo-β-N-acetylglucosaminidase A activity, and to a method for producing a polypeptide possessing endo-β-N-acetylglucosaminidase A activity by the use of the DNA.

2. Discussion of the Related Art

In recent years, various physiological functions of the sugar chain moieties of molecules known as complex carbohydrates, such as glycoproteins and glycolipids, have drawn attention. At present, carbohydrate-decomposing enzymes serve as very useful tools for elucidation of the structure and biological activity of sugar chains. Endo-β-N-acetylglucosaminidase, in particular, catalyzes the reaction in which the GlcNAcβ1-4GlcNAc bond of di-N-acetylchitobiose at the reduction end of the N-linked sugar chain of glycoproteins is broken to cut off the sugar chain from the protein and leave N-acetylglucosamine on the protein side. Endo-β-N-acetylglucosaminidase has further been used for structural or functional analysis of glycoproteins.

In addition, some forms of endo-β-N-acetylglucosaminidase are known to catalyze sugar chain rearrangement reactions; endo-β-N-acetylglucosaminidase A from the *Arthrobacter protoformiae* AKU 0647 strain (hereinafter also referred to as Endo-A), in particular, has been reported to possess very potent sugar chain rearrangement activity (Japanese Patent Laid-Open No. 5-64594). Specifically, Endo-A efficiently catalyzes the reaction in which the N-binding oligomannose type sugar chain of glycoproteins is cut out and transferred to an acceptor carbohydrate or complex carbohydrate. The Endo-A enzyme is therefore very useful not only for the structural analysis of sugar chains of glycoproteins but also for other purposes such as modification of sugar chains of complex carbohydrates, and preparation of neoglycoproteins.

A known form of Endo-A is derived from *Arthrobacter protoformiae* [Applied and Environmental Microbiology, 55, 3107–3112 (1989)].

However, in the method in which *Arthrobacter protoformiae* is cultured to obtain Endo-A, proteases and other glycosidases are also produced. It has been difficult to separate and purify these co-present enzymes from Endo-A. Also, to induce Endo-A enzyme production, ovalbumin or a sugar peptide thereof must be added to the culture medium. There has therefore been a need for the development of a method enabling the production of highly pure Endo-A at low cost.

Although purification of Endo-A from *Arthrobacter protoformiae* is already known [Applied and Environmental Microbiology, 55, 3107–3112 (1989)], there has been no knowledge regarding the amino acid sequence or gene structure of Endo-A, and hence there is no method of Endo-A production by gene engineering.

SUMMARY OF THE INVENTION

An object of the present invention is to provide a DNA having a nucleotide sequence encoding a polypeptide possessing Endo-A activity.

Another object of the present invention is to provide a recombinant DNA containing the DNA encoding a polypeptide possessing Endo-A activity.

Another object of the present invention is to provide an expression vector comprising the above recombinant DNA as an insert.

Another object of the present invention is to provide a transformant harboring the above expression vector.

Another object of the present invention is to provide an advantageous method for producing a polypeptide possessing Endo-A activity on an industrial scale using the DNA of the present invention.

In order to elucidate the amino acid sequence of Endo-A and the nucleotide sequence encoding Endo-A, the present inventors conducted intensive studies with an Endo-A producing bacterial strain (*Arthrobacter protoformiae* AKU 0647) and have succeeded in establishing the entire nucleotide sequence of the gene and the amino acid sequence of Endo-A. The present inventors have also succeeded in developing an advantageous method for industrial scale production of Endo-A using the Endo-A gene. Based upon these facts, the present invention has been completed.

In one embodiment, the present invention relates to an isolated or recombinant DNA comprising a nucleotide sequence encoding a polypeptide possessing Endo-A activity or functionally equivalent variants thereof.

In another embodiment, the present invention relates to an expression vector which comprises the DNA of the present invention having a nucleotide sequence encoding a polypeptide possessing Endo-A activity or functionally equivalent variant, wherein the expression vector is capable of propagating in a procaryotic or eucaryotic cell.

In another embodiment, the present invention relates to a cell of a procaryote or eucaryote transformed with an expression vector of the present invention.

In still another embodiment, the present invention relates to a method for producing a polypeptide possessing Endo-A activity or functionally equivalent variants thereof, comprising the steps of:

(a) cultivating a transformant obtained by introducing an expression vector into a host cell, the expression vector containing a DNA of the present invention; and (b) recovering the polypeptide possessing Endo-A activity or functionally equivalent variants thereof from the culture obtained in Step (a).

The entire amino acid sequence of Endo-A and the nucleotide sequence of the gene encoding the enzyme have first been provided by the present invention, thereby enabling an advantageous, industrial-scale production of a polypeptide possessing Endo-A activity using recombinant DNA technology.

DETAILED DESCRIPTION OF THE INVENTION

Figure 1:
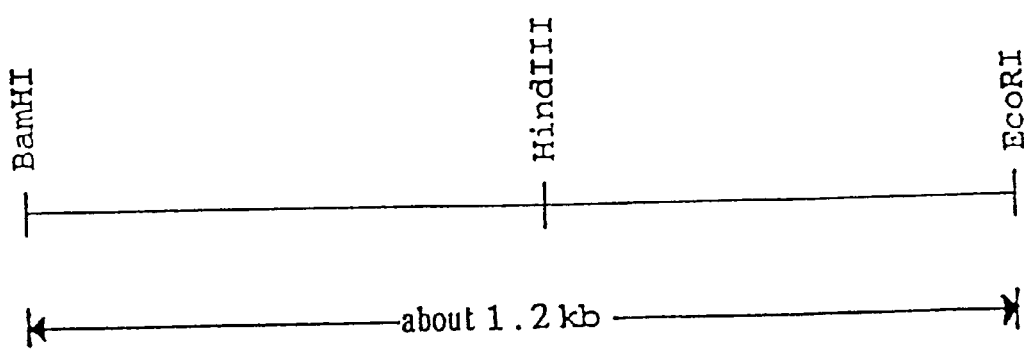
FIG. 1 shows a restriction map of the DNA fragment amplified by PCR.

The term endo-β-N-acetylglucosaminidase A as used herein is defined as possessing the following physicochemical properties described in Applied and Environmental Microbiology, 55, 3107–3112 (1989):

1. Action

Acts on the N-linked sugar chain of glycoproteins to break the GlcNAcβ1-4GlcNAc bond of di-N-acetylchitobiose at the reduction end of the sugar chain.

2. Substrate Specificity

Acts on oligomannose type sugar chains, glycopeptides and glycoproteins but not on complex sugar chains.

3. Optimum pH and pH Stability

Optimum pH is between 5.0 and 11.0; the enzyme is stable in the pH range from 5.0 to 7.0.

4. Optimum Temperature and Temperature Stability

Optimum temperature is 60° C.; the enzyme is stable up to 60° C.

The term "a polypeptide possessing Endo-A activity" as used herein includes not only native Endo-A but also its variations due to modification of amino acid sequence by, for example, deletion, substitution, insertion, or addition of amino acid residue(s), as long as they retain Endo-A activity.

"Native Endo-A" as used herein includes, but is not limited to, those produced by Arthrobacter strains. Also included are those derived from other microorganisms, such as other bacteria, yeasts, Actinomycetes, fungi, Ascomycetes, and Basidiomycetes, and those derived from plants and animal cells.

The term "functionally equivalent variant" as used herein is defined as follows:

A naturally-occurring protein can undergo amino acid deletion, insertion, addition, substitution and other variations in its amino acid sequence due to modifications, etc. of the protein itself in vivo or during purification, as well as due to polymorphism and mutation of the gene encoding it. It is a well-known fact that there are some such polypeptides which are substantially equivalent to variation-free proteins in terms of physiological or biological activity. A polypeptide structurally different from the corresponding protein, but having no significant functional difference from the protein is referred to as a functionally equivalent variant.

The same applies to polypeptides prepared by artificially introducing such variations into the amino acid sequence of a protein. Although more diverse variants can be thus obtained, the resulting variants are construed as functionally equivalent variants, as long as their physiological activity is substantially equivalent to that of the original variation-free protein.

For example, the methionine residue at the N-terminus of a protein expressed in *Escherichia coli* is reportedly often removed by the action of methionine aminopeptidase, but some such expressed proteins have the methionine residue and others do not. However, the presence or absence of the methionine residue does not affect protein activity in most cases. It is also known that a polypeptide resulting from replacement of a particular cysteine residue with serine in the amino acid sequence of human interleukin 2 (IL-2) retains IL-2 activity [Science, 224, 1431 (1984)].

In addition, in producing a protein by gene engineering, the desired protein is often expressed as a fused protein. For example, the N-terminal peptide chain derived from another protein is added to the N-terminus of the desired protein to enhance the expression of the desired protein, or purification of the desired protein is facilitated by adding an appropriate peptide chain to the N- or C-terminus of the desired protein, expressing the protein, and using a carrier showing affinity for the peptide chain added.

Also, with regards to a codon (triplet base combination) determining a particular amino acid on the gene, 1 to 6 kinds of codons are known to exist for each amino acid. Therefore, there can be a large number of genes encoding an amino acid sequence, depending on the amino acid sequence. In nature, genes are not stable, and it is not rare for genes to undergo nucleic acid variation. A variation on the gene may not affect the amino acid sequence to be encoded (silent variation); in this case, it can be said that a different gene encoding the same amino acid sequence has been generated. The possibility is therefore not negligible that even when a gene encoding a particular amino acid sequence is isolated, a variety of genes encoding the same amino acid sequence are produced after many generations of the organism containing it.

Moreover, it is not difficult to artificially produce a variety of genes encoding the same amino acid sequence by means of various gene engineering techniques.

For example, when a codon used in the natural gene encoding the desired protein is low in availability in the host used to produce the protein by gene engineering, the amount of protein expressed is sometimes insufficient. In this case, expression of the desired protein is enhanced by artificially converting the codon into another one of high availability in the host without changing the amino acid sequence encoded. Thus, it is of course possible to artificially produce a variety of genes encoding a particular amino acid sequence. Such artificially produced different polynucleotides are therefore included in the scope of the present invention, as long as an amino acid sequence disclosed herein is encoded.

Additionally, a polypeptide resulting from at least one change, such as deletion, addition, insertion or substitution, of one or more amino acid residues in the amino acid sequence of the desired protein commonly possesses an activity functionally equivalent to that of the desired protein; DNAs encoding such polypeptides are also included in the scope of the present invention, whether isolated from natural sources or produced artificially.

In general, nucleotide sequence of DNAs encoding functionally equivalent polypeptides often show high homology to each other. DNAs capable of hybridizing to a DNA for the present invention, and encoding a polypeptide possessing Endo-A activity, are therefore also included in the scope of the present invention.

The present invention is hereinafter described in detail with reference to Endo-A derived from *Arthrobacter protoformiae* AKU 0647.

The strain *Arthrobacter protoformiae* AKU 0647 has been deposited at the National Institute of Bioscience and Human-Technology, Agency of Industrial Science and Technology of 1–3, Higashi 1-chome, Tsukuba-shi, Ibarakiken, Japan on Aug. 14, 1991 under the Budapest Treaty, as accession number FERM BP-4948.

1) First, *Arthrobacter protoformiae* AKU 0647 is cultured in accordance with the method described in Applied and Environmental Microbiology, 55, 3107–3112 (1989). Endo-A produced by the *Arthrobacter protoformiae* AKU 0647 is then isolated from the culture and purified.

2) Second, information regarding a partial amino acid sequence of the purified Endo-A is obtained. The partial amino acid sequence is determined over the region of 10 to 20 residues in the N-terminal amino acid sequence of Endo-A by directly subjecting the purified Endo-A to amino acid sequencing based on Edman degradation by a conventional method (Protein Sequencer 476A, produced by Applied Biosystems). Alternatively, it is effective to conduct amino acid sequencing for a purified peptide fragment obtained by subjecting the purified Endo-A to limited hydrolysis by the action of a protein hydrolase with high specificity, such as Achromobacter protease I or N-tosyl-L-phenylalanylchloromethylketone (TPCK)-trypsin, and separating and purifying the resulting peptide fragments by reversed-phase HPLC.

3) On the basis of the thus-obtained partial amino acid sequence information, the Endo-A gene is cloned. For this purpose, a commonly used PCR or hybridization method is employed.

a) On the basis of the partial amino acid sequence information, synthetic oligonucleotides are designed for use as Southern hybridization probes.

b) Separately, the genomic DNA of *Arthrobacter protoformiae* AKU 0647 is completely digested with the appropriate restriction enzymes and subjected to agarose gel electrophoresis, and the resulting fragments are blotted onto a nylon membrane by a conventional method.

c) Hybridization of the separated DNA fragments with the synthetic oligonucleotides designed on the basis of the partial amino acid sequence information is conducted under commonly used conditions. For example, the nylon membrane is blocked in a prehybridization solution containing salmon sperm DNA, and each $^{32}$P-labeled synthetic oligonucleotide is added, followed by overnight incubation. After the nylon membrane is washed, an autoradiogram is taken to detect a DNA fragment that hybridizes to the synthetic oligonucleotide probe. The DNA fragment corresponding to the band detected is extracted from the gel and purified.

d) The thus-obtained DNA fragment, which hybridizes to the synthetic oligonucleotide probe, is inserted into a plasmid vector by a commonly used method. Useful plasmid vectors include, but are not limited to, pUC18, pUC19, pUC119 and pTV118N.

e) The recombinant plasmid is then introduced to a host to transform the host. When the host is *Escherichia coli*, it may be of a wild strain or a variant strain, as long as it is capable of being transformed. This plasmid introduction can be achieved by a commonly used method, such as the method described at page 250 of the Molecular Cloning, A Laboratory Manual (T. Maniatis et al., Cold Spring Harbor Laboratory Press, 1982).

f) Next, a transformant harboring the desired DNA fragment is selected.

For this purpose, the characteristics of the plasmid vector are utilized. In the case of pUC19, for instance, colonies having a foreign gene introduced thereto are selected by selecting ampicillin-resistant colonies on an ampicillin-containing plate, or selecting ampicillin-resistant white colonies on a plate containing ampicillin, 5-bromo-4-chloro-3-indolyl-β-D-galactoside (X-Gal) and isopropyl-β-D-thiogalactopyranoside (IPTG).

g) The colony having a vector containing the desired DNA fragment is then selected out of the above population. This selection is achieved by using colony hybridization or plaque hybridization, chosen appropriately according to vector types. PCR methods are also applicable.

h) Once the vector containing the desired DNA fragment is selected, the nucleotide sequence of the desired DNA fragment inserted in this vector is determined by an ordinary method, such as the dideoxy chain terminator method [Proceedings of the National Academy of Sciences of the USA, 74, 5463 (1977)]. The thus-determined nucleotide sequence is compared with the N-terminal sequence, partial amino acid sequence, molecular weight, etc. of Endo-A, to determine whether the nucleotide is the entire or partial portion of the desired Endo-A gene. From the thus-obtained DNA fragment containing the Endo-A gene, the structure of the Endo-A gene and the entire amino acid sequence of Endo-A are determined.

i) When the vector containing the desired DNA fragment does not contain the full-length Endo-A gene, the desired full-length Endo-A gene can be obtained by digesting the genomic DNA of *Arthrobacter protoformiae* AKU 0647 with other restriction enzymes, obtaining the lacking portion from the digests by hybridization, etc. using a part of the DNA fragment obtained above as a probe, as described above, and then joining the lacking portion.

Attempts to clone the Endo-A gene derived from *Arthrobacter protoformiae* AKU 0647 were made in order to obtain the desired gene by carrying out the PCR method using oligonucleotide primers designed on the boxes of the following information on partial amino acid sequences, but all failed to clone the desired gene.

In consideration of these facts, the present inventors made extensive investigation, and first found that a portion of the desired Endo-A gene can be amplified by using particular synthetic oligonucleotides designed and synthesized on the basis of an internal partial amino acid sequence of Endo-A as primers for PCR which uses genomic DNA as templates.

The present invention is hereinafter described in more detail. First, using synthetic oligonucleotide primers designed on the basis of partial amino acid sequence information and the genomic DNA of the *Arthrobacter protoformiae* AKU 0647 strain as a template, PCR is carried out to yield the desired gene fragment. Specifically, oligonucleotide primer 1 (SEQ ID NO:6) designed from the N-terminal amino acid sequence A-23 (SEQ ID NO:5), oligonucleotide primer 2 (SEQ ID NO:8) designed from the partial amino acid sequence A-46 (SEQ ID NO:7), oligonucleotide primer 3 (SEQ ID NO:10) designed from the partial amino acid sequence A-20 (SEQ ID NO:9), and oligonucleotide primer 4 (SEQ ID NO:12) designed from the partial amino acid sequence A-12 (SEQ ID NO:11), are synthesized. To facilitate the determination of the nucleotide sequence of the amplification product, a BamHI site has been added to the 5' end side of primer 1, and an EcoRI site to the 5' end sides of the other primers.

PCR is conducted in accordance with the method described in "PCR Technology", edited by Erlich H. A., published by Stockton Press in 1989, using the Gene Amp Reagent Kit (produced by Perkin-Elmer Cetus Instruments), for instance. The reaction is carried out 30 cycles at 94° C. for 1 minute, 49° C. for 1 minute and 30 seconds and 72° C. for 1 minute and 30 seconds each. After a first PCR is conducted with a combination of primers 1 and 2 using the genomic DNA of the *Arthrobacter protoformiae* AKU 0647 strain as a template, a second PCR is conducted with a combination of primers 1 and 3 or a combination of primers 1 and 4 using a portion of the first reaction mixture; subsequent agarose gel electrophoresis analysis of the second reaction mixture fails to detect a clear band attributable to amplified DNA. An additional PCR with a combination of primers 1 and 4 yields a specific band attributable to amplified DNA in agarose gel electrophoresis. The amplified DNA fragments are subjected to base sequencing by a commonly used method, e.g., the dideoxy chain terminator method. A sequence corresponding to a partial amino acid sequence of Endo-A was detected, and a portion of the desired Endo-A gene is successfully obtained. Of course, by conducting an additional procedure of the hybridization method using the thus-obtained gene fragment as a probe, the gene encoding the full-length of Endo-A sequence can be cloned.

The thus-obtained entire nucleotide sequence of the gene for the Endo-A produced by *Arthrobacter protoformiae* AKU 0647 was determined as set forth in SEQ ID NO:2, and the entire amino acid sequence deduced therefrom was determined as set forth in SEQ ID NO:1. It should be noted that there are numerous nucleotide sequences corresponding to SEQ ID NO:1 in addition to the nucleotide sequence of SEQ ID NO:2, and all the DNAs having such nucleotide sequences are included in the scope of the present invention. The DNAs of the present invention also include the DNAs encoding a polypeptide having a portion of the amino acid sequence of SEQ ID NO:1 and still retaining Endo-A activity or functionally equivalent activity. DNAs having a portion of the nucleotide sequence set forth in SEQ ID NO:2 and encoding a polypeptide possessing Endo-A activity or functionally equivalent activity are also included in the scope of the present invention. Also included are DNAs capable of hybridizing to the DNAs as mentioned above and encoding a polypeptide possessing Endo-A activity or functionally equivalent activity.

Using the entire Endo-A gene whose entire nucleotide sequence has been determined as described above, or a portion thereof, as a probe for hybridization, DNA encoding a polypeptide possessing Endo-A activity and having high homology to the Endo-A gene can be selected from a genomic DNA or cDNA library derived from an organism other than *Arthrobacter protoformiae* AKU 0647. Hybridization can be conducted using commonly used conditions. For example, nylon membranes where the genomic DNA library or cDNA library obtained from an organism other than *Arthrobacter protoformiae* AKU 0647 is blotted are prepared. The nylon membrane is blocked at 65° C. in a prehybridization solution containing 6×SSC, 0.5% SDS, 5×Denhardt's solution and 100 µg/ml salmon sperm DNA, and each $^{32}$P-labeled synthetic oligonucleotide probe is added, which is followed by overnight incubation at 65° C. After the nylon membrane is washed once with 6×SSC at room temperature for 10 minutes, and once with 2×SSC containing 0.1% SDS at room temperature for 10 minutes, and once with 0.2×SSC containing 0.1% SDS at 45° C. for 30 minutes, an autoradiogram is taken to detect DNA fragments that hybridizes to the probe. Genes showing different degrees of homology can be obtained by changing washing and other conditions.

On the other hand, a primer for PCR reaction can be designed from the nucleotide sequence of the gene of the present invention. It is possible to detect a gene fragment highly homologous to the gene of the present invention or obtain the entire gene, by carrying out PCR using this primer.

For producing a polypeptide possessing Endo-A activity using the Endo-A gene of the present invention, the following method is advantageous.

First, a host is transformed with a vector containing the desired Endo-A gene. This transformant is then cultured under commonly used conditions to produce a polypeptide possessing Endo-A activity. As the case may be, the polypeptide is produced in the form of an inclusion body. Useful hosts include microorganisms, animal cells and plant cells.

It is advantageous to confirm expression by, for example, determining Endo-A activity. Activity can be determined by the method described in Applied and Environmental Microbiology, 55, 3107–3112(1989), using a recombinant *Escherichia coli* cell extract as an enzyme solution.

When the desired expression of Endo-A is noted, Endo-A can be efficiently produced by setting optimum conditions for Endo-A expression as to medium composition, medium pH, culturing temperature, amount of inducer used, timing of induction, culturing time, etc., in cases where the transformant is *Escherichia coli*.

Endo-A can be purified from the transformant culture by an ordinary method. The transformant, like *Escherichia coli*, intracellularly accumulates Endo-A during cultivation. The cultivated transformant cells are collected by centrifugation, disrupted by ultrasonication, or the like, and then subjected to centrifugation, etc. to yield a cell-free extract, which can be purified by common protein purification methods, such as salting-out and various chromatographies including ion exchange, gel filtration, hydrophobic and affinity chromatographies. Depending on the host-vector system used, the expression product is extracellularly secreted by the transformant; in this case, the product can be purified from the culture supernatant in the same manner as that described above.

When Endo-A is intracellularly produced by the transformant, various enzymes are also present in the cell, but purification of the Endo-A is very easy, because such enzymes are present in trace amounts, relative to the amount of Endo-A. When Endo-A is extracellularly secreted, medium components, etc. are also present. However, these co-present substances normally contain almost no protein components that can interfere with Endo-A purification; this is advantageous in that there is no need for the painstaking separation procedures for purification of Endo-A from the *Arthrobacter protoformiae* AKU 0647 culture.

When the host is *Escherichia coil*, the expression product is sometimes formed as an insoluble inclusion body. In this case, cells are collected by centrifugation after cultivation, disrupted by ultrasonication, or the like, then subjected to centrifugation, etc. to separate the insoluble fraction containing the inclusion body. After being washed, the inclusion bodies are solubilized with a commonly used protein solubilizer, such as urea or guanidine hydrochloride, followed by purification by various chromatographies, such as ion exchange, gel filtration, hydrophobic and affinity chromatographies, as necessary, after which a refolding treatment by dialysis or dilution is conducted to yield the desired polypeptide retaining Endo-A activity. This standard preparation may be purified by various chromatographies to yield a highly pure polypeptide possessing Endo-A activity.

The same procedures as those described above may be used for producing and purifying a functionally equivalent variant of the DNA mentioned above.

As described above, the present invention provides the primary structure of Endo-A produced by *Arthrobacter protoformiae* AKU 0647, and the gene structure thereof. The elucidation of the gene structure of the present invention permits the biotechnological production of a polypeptide possessing Endo-A activity or functionally equivalent variant thereof. By the use of the present method using recombinant DNA technology, a highly pure polypeptide possessing Endo-A activity or a functionally equivalent variant thereof can be produced at low cost.

EXAMPLES

The following examples illustrate the present invention but are not intended to limit the invention in any manner.

Example 1. Cloning of Endo-A Structural Gene
(1) Extraction and Purification of Genomic DNA

*Arthrobacter protoformiae* AKU 0647 (FERM BP-4948), an Endo-A producer, was inoculated to 10 ml of a medium containing 0.5% yeast extract, 0.5% peptone and 0.5% NaCl, pH 7.5, and pre-cultured at 28° C. for 18 hours, after which 10 ml of the culture broth was transferred to each of five conical flasks each containing 100 ml of the same medium as above, and subjected to shaking culture for 24 hours. After completion of the cultivation, the culture broth was centrifuged to collect cells, which were then twice washed with a saline-EDTA solution (0.15 M NaCl, 0.1 M EDTA, pH 8.0) and suspended in 20 ml of a saline-EDTA solution, after which 0.5 ml of a lysozyme solution [dissolved at a concentration of 20 mg/ml in a saline-TE solution (0.1 M NaCl, 10 mM EDTA, 0.1 M Tris-HCl, pH 8.0)] was added, followed by shaking at 37° C. for 10 minutes. Subsequently, 5 ml of a 5% SDS solution (dissolved in saline-TE solution) was added. After the mixture was shaken at 60° C. for 20 minutes, 130 $\mu$l of proteinase K (10 mg/ml) was added (final concentration 50 $\mu$g/ml), followed by incubation at 37° C. for 3 hours. The reaction mixture was then cooled to room temperature and gently stirred in the presence of an equal volume of phenol saturated with TE buffer (10 mM Tris-HCl, 1 mM EDTA, pH 8.0). After centrifugation at 8000 rpm for 20 minutes, the upper layer was collected (hereinafter referred to as phenol extraction). To the water layer, a 2-fold volume of cold ethanol was gradually added to precipitate DNA, which was then wound around a glass rod, washed with 70%, 80% and 90% cold ethanol solutions, and gently dried in air (hereinafter referred to as ethanol precipitation). This dry product was dissolved in 18 ml of 0.1×SSC [20×SSC (3 M NaCl, 0.3 M sodium citrate) used after dilution]; 2 ml of 10×SSC and 100 $\mu$l of RNase A (10 mg/ml) (final concentration 50 $\mu$g/ml) were added, followed by incubation at 37° C. for 1 hour. After completion of the reaction, deproteinization and ethanol precipitation were conducted. The resulting precipitate was dissolved in 2 ml of 0.1×SSC and dialyzed against TE buffer for 24 hours, then subjected to phenol/chloroform extraction, chloroform extraction and ethanol precipitation, followed by centrifugation to collect DNA, which was then dissolved in TE buffer to yield a genomic DNA solution. The concentration of the genomic DNA thus obtained was determined from its absorbance to be 509 $\mu$g/ml. Agarose electrophoresis demonstrated that the genomic DNA had a size not shorter than 24 kb.

(2) Determination of Partial Amino Acid Sequence of Endo-A

Endo-A as purified by the method described in Applied and Environmental Microbiology, 55, 3107–3112 (1989) was directly subjected to amino acid sequencing by gas phase Edman degradation to determine the N-terminal amino acid sequence A-23 (SEQ ID NO:5). After being pyridylethylated [1 nmol of endo-A protein was applied to a desalting column (Fast Desalting Column PC3.2/10, Pharmacia), previously equilibrated with 450 mM N-ethylmorpholine/formate buffer, pH 8.5, and eluted with the same buffer; the resulting eluate was collected in a glass vial and concentrated to dryness; separately, 10 $\mu$l of pyridine, 2 $\mu$l of 4-vinylpyridine, 2 $\mu$l of tri-N-butylphosphine and 10 $\mu$l of water were placed in a glass test tube larger in diameter than the vial; the sample-containing glass vial was placed in this glass test tube; after the glass test tube was sealed, a reaction was carried out at 100° C. for 5 minutes; after completion of the reaction, the glass vial was taken out from the test tube and thoroughly dried; the resulting pyridylethylated product was used for lysylendopeptidase digestion], the enzyme protein was digested with lysylendopeptidase [40 $\mu$l of a 10 mM Tris-HCl buffer (pH 7.5) containing 4 M urea, 50 $\mu$l of a 10 mM Tris-HCl buffer (pH 7.5), 10 $\mu$l of 0.1 M calcium chloride, and 2 pmol of lysylendopeptidase were added to the glass vial, followed by overnight reaction at 37° C.]; from the resulting digest, a peptide fragment was separated and purified by HPLC (Smart System, produced by Pharmacia; column, mRPC C2/C18, SC2.1/10; flow rate, 1 ml/min; eluent A, 0.1% trifluoroacetic acid solution; eluent B, acetonitrile containing 0.1% trifluoroacetic acid; elution was conducted on a density gradient from 0% of eluent B at the time of sample application to 10% of eluent B at the time of completion of sample application, after which the eluent B concentration was increased to 60% over an 85-minute period). Each peptide fraction was subjected to amino acid sequencing to determine the partial amino acid sequences A-46 (SEQ ID NO:7), A-20 (SEQ ID NO:9), and A-12 (SEQ ID NO:11).

(3) Preparation of Gene Library of *Arthrobacter protoformiae* AKU 0647 Strain

To 10 $\mu$l of the genomic DNA (509 $\mu$g/ml) prepared in (1) above, 8 units of the restriction enzyme Sau3AI (produced by Takara Shuzo) were added to make a total volume of 50 $\mu$l, after which the genomic DNA was digested at 37° C. for 20, 30, 40 and 60 seconds. The reaction was terminated at each time point by adding 15 $\mu$l of 100 mM EDTA (pH 8.0) and heating at 60° C. for 20 minutes.

Agarose gel electrophoresis demonstrated that this genomic DNA was partially digested from about 24 kb to about 1 kb with the progress of the reaction.

The above partial digest solutions were combined and subjected to agarose electrophoresis; DNA fragments of about 4 to 23 kb size were cut out, followed by DNA recovery using the EASY TRAP (produced by Takara Shuzo) and subsequent ethanol precipitation; the resulting precipitate was dissolved in 10 $\mu$l of TE buffer.

Using a ligation kit (produced by Takara Shuzo), the λEMBL3 arm (produced by STRATAGENE) and each of the about 4 to 23 kb DNA fragments obtained were allowed to react at 16° C. for 10 minutes in the composition shown in Table 1 to yield a recombination vector.

TABLE 1

| λEMBL3 arm | 0.5 $\mu$L (0.5 $\mu$g) |
| DNA fragment | 8.5 $\mu$L |
| 3M NaCl | 1.0 $\mu$L |
| Solution B (in kit) | 10 $\mu$L |
| Total | 20 $\mu$L |

This reaction mixture was subjected to ethanol precipitation; the resulting precipitate was dissolved in 4 $\mu$l of TE buffer to yield a ligation DNA solution, which was then subjected to in vitro packaging using the Gigapack II Gold Packaging Extract (produced by STRATAGENE).

The phage liquid prepared by the in vitro packaging, 1, 5 or 10 $\mu$l each, was added to 600 $\mu$l of an *E. coli* P2392 suspension [prepared by culturing the strain in 50 ml of TB medium (0.5% NaCl, 1.0% peptone, pH 7.4) containing 10 mM MgSO$_4$ and 0.2% maltose at 28° C. for 10 hours, collecting cells, and suspending the cells in 10 mM MgSO$_4$ to an absorbance (600 nm) of 0.5], followed by incubation at 37° C. for 15 minutes, to infect the strain with the phage.

Next, to 3 ml of top agar [NZY medium (0.5% NaCl, 0.5% yeast extract, 0.2% MgSO$_4$·7H$_2$O, 1.0% NZ amine), 0.7% agarose], previously incubated at 50° C., the above phage-infected liquid was added, followed by immediate mixing, after which the mixture was poured over bottom agar (NZY medium, 3% agar), previously incubated at 37° C., followed by incubation at 37° C. for 8 hours. After confirming that the plaques on the plate became 0.5 to 1.0 mm in size, they were stored in a refrigerator (4° C.).

The plaques appeared on the medium was used as a gene library. Out of the resulting plaques, 6 were randomly picked up and examined for DNA inserts. Four of the 6 clones were found to contain an about 10 kb DNA insert.

Also, the same procedure was carried out to yield a gene library consisting of about 10000 clones.

(4) Cloning of DNA Fragment Containing Endo-A Gene

Primer 1 (SEQ ID NO:6), designed from the N-terminal amino acid sequence A-23 (SEQ ID NO:5) determined in (2) above, primer 2 (SEQ ID NO:8), designed from the partial amino acid sequence A-46 (SEQ ID NO:7), primer 3 (SEQ ID NO:10), designed from the partial amino acid sequence A-20 (SEQ ID NO:9), and primer 4 (SEQ ID NO:12), designed from the partial amino acid sequence A-12 (SEQ ID NO:11), were synthesized. To facilitate the determination of the nucleotide sequence of the amplification product, a BamHI site has been added to the 5' end side of primer 1, and an EcoRI site to the 5' end side of the other primers.

Using these primers, PCR was conducted with the genomic DNA of the *Arthrobacter protoformiae* AKU 0647 strain as a template, in accordance with the method described in "PCR Technology", edited by Erlich H. A., published by Stockton Press in 1989, using the Gene Amp Reagent Kit (produced by Perkin-Elmer Cetus Instruments). The reaction was conducted 30 cycles at 94° C. for 1 minute, 49° C. for 1 minute and 30 seconds and 72° C. for 1 minute and 30 seconds each.

This PCR resulted in specific amplification of a DNA fragment with a combination of primer 1 (SEQ ID NO:6) and primer 4 (SEQ ID NO:12) in a single operation.

The DNA fragment (about 1.2 kb) amplified with the combination of primers 1 and 4 was cut out, followed by DNA collection using the EASY TRAP (produced by Takara Shuzo). This DNA fragment was digested with the restriction enzymes EcoRI and BamHI (both produced by Takara Shuzo) and ligated at the EcoRI and BamHI sites of the plasmid pBluescript (produced by STRATAGENE) using a ligation kit (produced by Takara Shuzo).

To draw the restriction map for the amplified DNA fragment (about 1.2 kb), the fragment was digested with the restriction enzyme HindIII (produced by Takara Shuzo), which revealed that one HindIII site was present near the center of the DNA fragment (FIG. 1).

Next, this amplified DNA fragment was analyzed by the dideoxy chain terminator method to determine the nucleotide sequences from both the BamHI and EcoRI sites. In addition, the nucleotide sequences of both sides of the only HindIII site at the center of this amplified DNA fragment were also determined by the dideoxy chain terminator method. The nucleotide sequence on the BamHI site side is shown in SEQ ID NO:13 in the sequence listing; the nucleotide sequence on the EcoRI site side is shown in SEQ ID NO:14 in the sequence listing; the nucleotide sequence on the BamHI site side of the HindIII site is shown in SEQ ID NO:15 in the sequence listing; the nucleotide sequence on the EcoRI site side of the HindIII site is shown in SEQ ID NO:16 in the sequence listing.

As a result, in addition to the sequences of primers 1 and 4, a sequence corresponding to a partial amino acid sequence of Endo-A was found in the sequence determined; a portion of the desired Endo-A gene was successfully obtained.

(5) Cloning of Endo-A Gene

Next, using the DNA fragment (about 1.2 kb) obtained in (4) above as a probe, the gene library prepared in (3) above was screened.

First, 480 μg of the amplified DNA fragment (about 1.2 kb) was labeled using the ECL random prime labeling system (produced by Amersham Corporation), as directed in the system protocol.

Using this labeled DNA fragment as a probe, plaque hybridization with the gene library prepared in (3) above was carried out. Plaque hybridization was conducted by the method described in the instruction manual for the ECL random prime labelling system and the method described in "Molecular Cloning—A Laboratory Manual—, 2nd edition," edited by Maniatis et al., Chapter 2, pp. 108–122, published by Cold Spring Harbor Laboratory Press in 1989. Specifically, a nylon membrane produced by Amersham Corporation (trade name Hybond-N+) was cut into plate pieces and marked with an about 1 mm groove to identify the nylon membrane orientation, and placed on a plate of the gene library prepared in (3) above. This plate was kept standing for 5 minutes, after which the nylon membrane was slowly peeled from the plate, placed on filter paper, moistened with 0.5 M NaOH, with face contacting the plate up, and kept standing for 5 minutes. This nylon membrane was then transferred onto dry filter paper to remove the water. The DNA was immobilized onto a nylon membrane using FUNA-UV-1-LINKER FS-800 (produced by Funakoshi). A filter for plaque hybridization was thus prepared. The filter thus prepared was subjected to prehybridization in a solution containing 5×SSC [1×SSC=solution of 8.77 g of NaCl and 4.41 g of sodium citrate in 1 l of water), 0.5% SDS, 100 μg/ml salmon sperm DNA and 5×Denhardt's (containing bovine serum albumin, polyvinylpyrrolidone and Ficoll each at 0.1% concentration) at 60° C. for 1 hour, after which the DNA fragment labeled as above, as a labeled probe, was added to make a concentration of 5 ng/ml (the labeled probe was previously heated in boiling water for 5 minutes, then rapidly quenched in ice), followed by hybridization at 60° C. for 8 hours and 50 minutes.

Next, the filter was sequentially washed in 1×SSC containing 0.1% SDS at 60° C. for 15 minutes, in 0.5×SSC containing 0.1% SDS at 60° C. for 15 minutes, and in buffer A (0.1 M Tris-HCl, pH 7.5, 0.6 M NaCl) at 25° C. for 1 minute. Next, to further diminish the hybridization background, the plate was washed in the liquid block attached to the system diluted 20 times with buffer A at 25° C. for 30 minutes.

Next, an antibody reaction was conducted in a solution containing the HRP-labeled anti-fluorescein antibody attached to the system in a 1/1000 volume of buffer A (containing 0.5% BSA) at 25° C. for 30 minutes. Next, the plate was washed in buffer A containing 0.5% BSA at 25° C. for 30 minutes and in buffer A containing 0.1% Tween 20 at 25° C. for 10 minutes. The same procedure was carried out 3 times in total.

Next, in a solution consisting of a 1:1 mixture of the detection reagents 1 and 2 attached to the system, a detection reaction was carried out at 25° C. for 1 minute, after which this filter was exposed to light for 20 minutes in the same manner as that for autoradiography.

As a result, 13 positive plaques were obtained, each of which was suspended in 500 μl of SM buffer (0.58% NaCl, 0.2% MgSO$_4$·7H$_2$O, 50 mM Tris-HCl, pH 7.5, 0.01% gelatin), then kept standing at room temperature for 1 hour, followed by centrifugation. The resulting supernatant was collected as a phage liquid and stored at 4° C. after adding one drop of chloroform as a preservative.

Phage DNA was collected from the thus-obtained phage liquid. Using this phage DNA as a template, PCR was conducted with primer 1 (SEQ ID NO:6) and primer 4 (SEQ ID NO:12) under the conditions described in (4) above. As a result, 2 of the 13 DNA clones were confirmed to contain the expected about 1.2 kb DNA fragment by agarose gel electrophoresis.

To purify the two phage DNAs, the phage liquid prepared above, corresponding to this phage DNA, 1, 5 or 10 µl each, was added to 600 µl of an *E. coli* P2392 suspension [prepared by culturing the strain in 50 ml of TB medium (0.5% NaCl, 1.0% peptone, pH 7.4) containing 10 mM MgSO$_4$ and 0.2% maltose at 28° C. for 10 hours, collecting cells, and suspending the cells in 10 mM MgSO$_4$ to an absorbance (600 nm) of 0.5], followed by incubation at 37° C. for 15 minutes, to infect the strain with the phage liquid.

Next, to 3 ml of top agar [NZY medium (0.5% NaCl, 0.5% yeast extract, 0.2% MgSO$_4$·7H$_2$O, 1.0% NZ amine), 0.7% agarose], previously heated at 50° C., the above phage-infected liquid was added, followed by immediate mixing, after which the mixture was poured onto bottom agar (NZY medium, 3% agar), previously heated at 37° C., followed by incubation at 37° C. for 8 hours.

The plates on which single plaques appeared were each subjected to plaque hybridization under the same conditions as those described above. From the thus-obtained positive plaques, 2 plates per plaque were selected, and phage liquids were prepared in the same manner as above to yield phage DNA. Using each phage DNA as a template, PCR was conducted under the conditions shown in (4) above with primer 1 (SEQ ID NO:6) and primer 4 (SEQ ID NO:12); 3 of the 4 phage DNAs were confirmed to contain the expected about 1.2 kb DNA fragment by agarose gel electrophoresis.

To determine whether or not the phage DNAs obtained are identical, each was digested with the restriction enzymes BamHI and HindIII (both produced by Takara Shuzo); the same electrophoresis pattern was obtained from the two, while a different pattern was obtained from the other one.

A part of the desired Endo-A gene was thus successfully cloned. Of the two phage DNAs obtained (phage DNA 1 and phage DNA 10), phage DNA 1 was used for the following experiments, in view of simplicity in handling.

(6) Subcloning of Endo-A Gene

DNA clone 1, obtained in (5) above, was digested with each of the restriction enzymes ClaI, HindIII, PstI and SalI (all produced by Takara Shuzo) and subjected to agarose gel electrophoresis, after which hybridization was conducted at 60° C. for 12 hours by the method described in "Molecular Cloning—A Laboratory Manual—, 2nd edition, edited by Maniatis et al., Chapter 9, pp. 31–58, published by Cold Spring Harbor Laboratory Press in 1989," using the DNA fragment (about 1.2 kb) labeled in (5) above as a probe.

Figure 2:
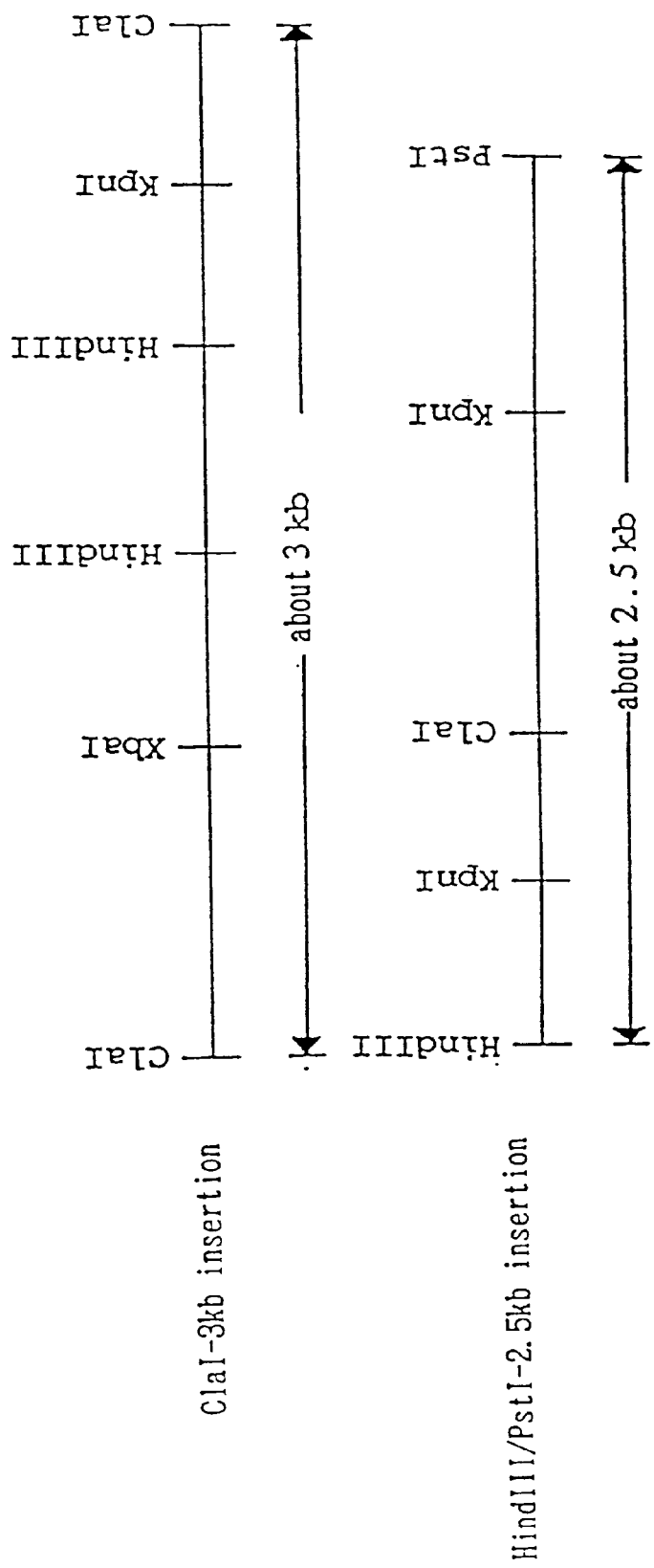
FIG. 2 shows restriction maps of 3 kb Cla I insertion fragment and 2.5 kb Hind III/Pst I insertion fragment.

As a result, the about 3 kb DNA fragment obtained by digestion with the restriction enzyme ClaI was hybridized to the DNA fragment (about 1.2 kb) labeled in (5) above. This about 3 kb DNA fragment showing hybridization was recovered and ligated to the ClaI site of pBluescript SK(−) (produced by STRATAGENE). This plasmid was designated as ClaI-3 kb. The restriction enzyme map for the inserts of ClaI-3 kb is shown in FIG. 2.

The nucleotide sequence of the insert in this plasmid was determined by the dideoxy chain terminator method. Although the sequences of primer 1 encoding N-terminal region and primer 4 were found in the insert but only an about 0.3 kb portion from the end of primer 4 in the direction to the C-terminus-coding region was contained. To obtain a DNA fragment encoding the entire C-terminal region, a HindIII-ClaI fragment (about 0.9 kb), the insert closest to the C-terminus-coding region in ClaI-3 kb was labeled in the same manner as in the method described in (5) above. Using this labeled fragment as a probe, DNA clone 1, obtained in (5) above, was digested with each of the restriction enzymes HindIII, KpnI, PstI, PvuII, HindIII-KpnI, HindIII-PstI and HindIII-PvuII and subjected to agarose gel electrophoresis, after which hybridization was conducted at 60° C. for 12 hours by the method described in "Molecular Cloning—A Laboratory Manual—, 2nd edition, edited by Maniatis et al., Chapter 9, pp. 31–58, published by Cold Spring Harbor Laboratory Press in 1989."

As a result, the about 2.5 kb DNA fragment obtained by digestion with HindIII-PstI was hybridized to this probe. This about 2.5 kb DNA fragment showing hybridization was collected and ligated to the HindIII-PstI site of pBluescript SK(−) (produced by STRATAGENE). This plasmid was designated as HindIII/PstI-2.5 kb. The restriction map for the inserts in HindIII/PstI-2.5 kb is shown in FIG. 2.

The nucleotide sequence of the insert in this plasmid was determined by the dideoxy chain terminator method; the sequence determined was found to contain the HindIII-ClaI fragment (about 0.9 kb) from ClaI-3 kb, with a termination codon on the 3' side.

By combining the plasmids HindIII/PstI-2.5 kb and ClaI-3 kb, the full length of the Endo-A gene can be known. An example nucleotide sequence of the open reading frame (ORF) for Endo-A is shown in SEQ ID NO:4 in the sequence listing; the amino acid sequence encoded by that nucleotide sequence is shown in SEQ ID NO:3 in the sequence listing. Also, on the basis of the finding regarding the N-terminal amino acid sequence A-23 (SEQ ID NO:5) of Endo-A obtained in (2) above, an example of nucleotide sequence encoding Endo-A is shown in SEQ ID NO:2 in the sequence listing; the amino acid sequence encoded by that nucleotide sequence is shown in SEQ ID NO:1 in the sequence listing.

Example 2. Construction of Endo-A Expression Plasmid (1) Construction of Plasmid Containing Full-Length Endo-A Gene The HindIII-ClaI fragment in the plasmid HindIII/PstI-2.5 kb was replaced with the insert in the plasmid ClaI-3 kb to yield the ClaI-PstI plasmid, which contains the gene encoding Endo-A in full length. The plasmid thus obtained, which contains the full-length Endo-A gene, was designated as pEACP.

The *E. coli* XL1-Blue strain transformed with pEACP is referred to as *Escherichia coli* XL1-Blue/pEACP. The *E. coli* XL1-Blue strain transformed with pEACP, with the designation *Escherichia coli* XL1-Blue/pEACP, has been deposited at the National Institute for Bioscience and Human-Technology, Agency of Industrial Science and Technology of 1–3, Higashi 1-chome, Tsukuba-shi, Ibarakiken, Japan on Oct. 5, 1995 under the Budapest Treaty, as accession number FERM BP-5581.

(2) Determination of Endo-A Activity

*Escherichia coli* XL1-Blue/pEACP was cultured at 37° C. for about 10 hours in 5 ml of 2×TY medium containing 100 µg/ml ampicillin. A portion of this culture broth was centrifuged; the resulting supernatant, as a crude enzyme solution, was subjected to Endo-A activity determination by the method described in Applied and Environmental Microbiology, 55, 3107–3112 (1989). Specifically, after the reaction was carried out at 37° C. for 1 hour with the composition shown in Table 2, an Endo-A activity of about 9 mU/ml was observed.

TABLE 2

| | | |
|---|---|---|
| 8 mM | Dansylated asparagine glycopeptide | 5 μL |
| 200 mM | Acetate buffer 8 pH 6.0) | 10 μL |
| | Crude enzyme solution | 5 μL |
| | Total | 20 μL |
| | Reaction stopper | 5 μL |

(3) Western Blotting of Endo-A

To determine whether or not the Endo-A in the crude Endo-A solution prepared from *Escherichia coli* XL1-Blue/pEACP in (2) above is identical with the endo-A from the *Arthrobacter protoformiae* AKU 0647 strain, western blotting was conducted by the method described in "Molecular Cloning—A Laboratory Manual—, 2nd edition, edited by Maniatis et al., Chapter 18, pp. 60–74, published by Cold Spring Harbor Laboratory Press in 1989." The Endo-A antibody used was prepared by the method described in "Molecular Cloning—A Laboratory Manual—, 2nd edition, edited by Maniatis et al., Chapter 18, pp. 3–17, published by Cold Spring Harbor Laboratory Press in 1989," using Endo-A purified by the method described in Applied and Environmental Microbiology 55, 3107–3112 (1989). The results are shown in FIG. 3, in which lane 1 shows the results obtained using about 15 ng of the Endo-A prepared from the *Arthrobacter protoformiae* AKU 0647 strain, lane 2 shows the results obtained using about 2 μg of the protein of the crude enzyme solution prepared from *Escherichia coli* XL1-Blue/pEACP in (2) above.

Figure 3:
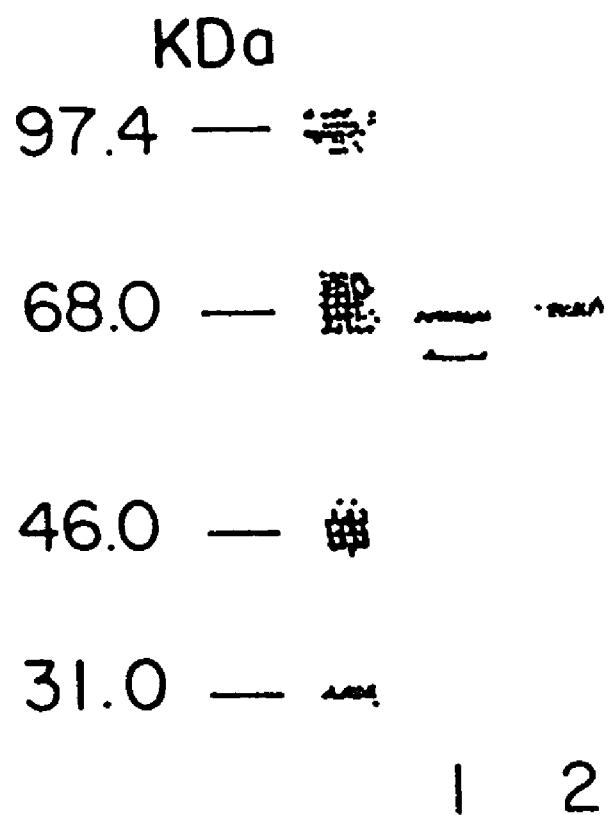
FIG. 3 shows the results of western blotting of endo-A.

As seen from FIG. 3, the Endo-A of *Escherichia coli* XL1-Blue/pEACP was confirmed to be identical with the Endo-A from the *Arthrobacter protoformiae* AKU 0647 strain.

Other modifications of the above described embodiments of the invention which are obvious to those skilled in the art are intended to be within the scope of the following claims.

What is claimed is:

1. An isolated DNA encoding a polypeptide possessing endo-β-N-acetylglucosaminidase A activity, the isolated DNA being selected from the group consisting of:
   (a) a DNA having the nucleotide sequence of SEQ ID NO:2;
   (b) a DNA having a nucleotide sequence encoding the amino acid sequence of SEQ ID NO:1; and
   (c) a DNA sequence hybridizing to (a) or (b) under conditions of using a solution containing 6×SSC, 0.5% SDS, 5×Denhardt's solution and 100 μg/ml of salmon sperm DNA, and incubating overnight at 65° C.

2. The isolated DNA according to claim 1, wherein the polypeptide is derived from a strain of the genus Arthrobacter.

3. The isolated DNA according to claim 2, wherein the polypeptide is derived from *Arthrobacter protoformiae* AKU 0647 strain (FERM BP-4948).

4. A recombinant DNA which comprises a DNA sequence of any one of claims 1 to 3.

5. A vector which comprises the recombinant DNA of claim 4.

6. The vector according to claim 5, wherein said recombinant DNA is operably linked to a promoter.

7. A cell of a prokaryote or eucaryote transformed with the vector of claim 5.

8. A method for producing a polypeptide possessing endo-β-N-acetylglucosaminidase A activity, comprising the steps of:
   (a) culturing the cell of claim 7; and
   (b) recovering the polypeptide possessing endo-β-N-acetylglucosaminidase A activity from the culture obtained in Step (a).

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH:  621 amino acids
      (B) TYPE:  amino acid
      (C) STRANDEDNESS:  single
      (D) TOPOLOGY:  linear (ii) MOLECULE TYPE: peptide (xi) SEQUENCE DESCRIPTION:   SEQ ID NO:1:

```
Ser Thr Tyr Asn Gly Pro Leu Ser Ser His Trp Phe Pro Glu Glu
 1               5                  10                  15

Leu Ala Gln Trp Glu Pro Asp Ser Asp Pro Asp Ala Pro Phe Asn
                20                  25                  30

Arg Ser His Val Pro Leu Glu Pro Gly Arg Val Ala Asn Arg Val
                35                  40                  45

Asn Ala Asn Ala Asp Lys Asp Ala His Leu Val Ser Leu Ser Ala
                50                  55                  60

Leu Asn Arg His Thr Ser Gly Val Pro Ser Gln Gly Ala Pro Val
                65                  70                  75

Phe Tyr Glu Asn Thr Phe Ser Tyr Trp His Tyr Thr Asp Leu Met
                80                  85                  90

Val Tyr Trp Ala Gly Ser Ala Gly Glu Gly Ile Ile Val Pro Pro
                95                 100                 105

Ser Ala Asp Val Ile Asp Ala Ser His Arg Asn Gly Val Pro Ile
               110                 115                 120

Leu Gly Asn Val Phe Phe Pro Pro Thr Val Tyr Gly Gly Gln Leu
               125                 130                 135

Glu Trp Leu Glu Gln Met Leu Glu Gln Glu Glu Asp Gly Ser Phe
               140                 145                 150

Pro Leu Ala Asp Lys Leu Leu Glu Val Ala Asp Tyr Tyr Gly Phe
               155                 160                 165

Asp Gly Trp Phe Ile Asn Gln Glu Thr Glu Gly Ala Asp Glu Gly
               170                 175                 180
```

```
Thr Ala Glu Ala Met Gln Ala Phe Leu Val Tyr Leu Gln Glu Gln
                185                 190                 195

Lys Pro Glu Gly Met His Ile Met Trp Tyr Asp Ser Met Ile Asp
            200                 205                 210

Thr Gly Ala Ile Ala Trp Gln Asn His Leu Thr Asp Arg Asn Lys
        215                 220                 225

Met Tyr Leu Gln Asn Gly Ser Thr Arg Val Ala Asp Ser Met Phe
    230                 235                 240

Leu Asn Phe Trp Trp Arg Asp Gln Arg Gln Ser Asn Glu Leu Ala
245                 250                 255

Gln Ala Leu Gly Arg Ser Pro Tyr Asp Leu Tyr Ala Gly Val Asp
                260                 265                 270

Val Glu Ala Arg Gly Thr Ser Thr Pro Val Gln Trp Glu Gly Leu
            275                 280                 285

Phe Pro Glu Gly Glu Lys Ala His Thr Ser Leu Gly Leu Tyr Arg
        290                 295                 300

Pro Asp Trp Ala Phe Gln Ser Ser Glu Thr Met Glu Ala Phe Tyr
    305                 310                 315

Glu Lys Glu Leu Gln Phe Trp Val Gly Ser Thr Gly Asn Pro Ala
320                 325                 330

Glu Thr Asp Gly Gln Ser Asn Trp Pro Gly Met Ala His Trp Phe
                335                 340                 345

Pro Ala Lys Ser Thr Ala Thr Ser Val Pro Phe Val Thr His Phe
            350                 355                 360

Asn Thr Gly Ser Gly Ala Gln Phe Ser Ala Glu Gly Lys Thr Val
        365                 370                 375

Ser Glu Gln Glu Trp Asn Asn Arg Ser Leu Gln Asp Val Leu Pro
    380                 385                 390

Thr Trp Arg Trp Ile Gln His Gly Gly Asp Leu Glu Ala Thr Phe
395                 400                 405

Ser Trp Glu Glu Ala Phe Glu Gly Gly Ser Ser Leu Gln Trp His
                410                 415                 420

Gly Ser Leu Ala Glu Gly Glu His Ala Gln Ile Glu Leu Tyr Gln
            425                 430                 435

Thr Glu Leu Pro Ile Ser Glu Gly Thr Ser Leu Thr Trp Thr Phe
        440                 445                 450

Lys Ser Glu His Gly Asn Asp Leu Asn Val Gly Phe Arg Leu Asp
    455                 460                 465

Gly Glu Glu Asp Phe Arg Tyr Val Glu Gly Glu Gln Arg Glu Ser
470                 475                 480

Ile Asn Gly Trp Thr Gln Trp Thr Leu Pro Leu Asp Ala Phe Ala
                485                 490                 495

Gly Gln Thr Ile Thr Gly Leu Ala Phe Ala Ala Glu Gly Asn Glu
            500                 505                 510

Thr Gly Leu Ala Glu Phe Tyr Ile Gly Gln Leu Ala Val Gly Ala
        515                 520                 525

Asp Ser Glu Lys Pro Ala Ala Pro Asn Val Asn Val Arg Gln Tyr
    530                 535                 540

Asp Pro Asp Pro Ser Gly Ile Gln Leu Val Trp Glu Lys Gln Ser
545                 550                 555

Asn Val His His Tyr Arg Val Tyr Lys Glu Thr Lys His Gly Lys
                560                 565                 570

Glu Leu Ile Gly Thr Ser Ala Gly Asp Arg Ile Tyr Leu Glu Gly
```

-continued

```
                       575                 580                 585
Leu Val Glu Glu Ser Lys Gln Asn Asp Val Arg Leu His Ile Glu
                590                 595                 600

Ala Leu Ser Glu Thr Phe Val Pro Ser Asp Ala Arg Met Ile Asp
                605                 610                 615

Ile Lys Ser Gly Ser Phe
                620
```

(2) INFORMATION FOR SEQ ID NO:2:

(i) SEQUENCE CHARACTERISTICS:
        (A) LENGTH: 1863 base pairs
        (B) TYPE: nucleic acid
        (C) STRANDEDNESS: double
        (D) TOPOLOGY: linear (ii) MOLECULE TYPE: genomic DNA (vi) ORIGINAL SOURCE:
        (A) ORGANISM: Arthrobacter protoformiae
        (B) STRAIN: AKU 0647

(xi) SEQUENCE DESCRIPTION: SEQ ID NO:2:

```
TCTACGTACA ACGGCCCGCT GTCCTCCCAT TGGTTTCCAG AGGAACTTGC CCAATGGGAA    60
CCAGACAGTG ATCCAGACGC ACCCTTTAAC AGAAGCCATG TTCCGCTGGA ACCAGGCCGC   120
GTTGCGAATA GGGTAAATGC TAATGCAGAC AAGGACGCAC ACCTTGTTTC GTTGTCCGCG   180
CTAAACAGGC ATACATCAGG TGTTCCATCG CAAGGAGCGC CAGTTTTCTA TGAAAATACG   240
TTCAGCTATT GGCATTATAC AGATTTGATG GTTTATTGGG CTGGTTCAGC TGGCGAAGGC   300
ATTATCGTTC CGCCAAGTGC CGATGTCATT GATGCATCGC ACCGAAATGG GGTGCCGATT   360
TTAGGAAATG TGTTCTTCCC GCCGACGGTT TATGGAGGGC AGCTAGAGTG CTAGAACAA    420
ATGTTAGAGC AAGAGGAGGA CGGTTCATTC CCCCTTGCTG ACAAATTGCT AGAAGTCGCA   480
GACTATTATG GGTTTGACGG CTGGTTTATT AACCAAGAAA CAGAAGGGGC AGACGAAGGA   540
ACAGCCGAAG CCATGCAAGC TTTTCTCGTT TATTTGCAGG AACAAAAGCC AGAAGGCATG   600
CACATCATGT GGTATGACTC GATGATTGAT ACAGGGGCGA TCGCCTGGCA AAACCATTTA   660
ACGGATCGAA ATAAAATGTA CTTGCAAAAT GGCTCGACCC GCGTCGCTGA CAGCATGTTT   720
TTGAACTTTT GGTGGCGTGA CCAGCGCCAA TCGAACGAAT TGGCACAAGC ACTTGGCAGG   780
TCTCCGTATG ACCTCTATGC CGGAGTGGAT GTGGAAGCAC GAGGGACAAG TACCCCTGTT   840
CAGTGGGAAG GCCTGTTTCC TGAAGGAGAA AAGGCGCATA CATCACTCGG GTTATACCGT   900
CCAGATTGGG CATTTCAGTC AAGTGAAACA ATGGAAGCGT TTATGAAAA  AGAACTACAA   960
TTTTGGGTTG GCTCGACAGG AAATCCAGCC GAAACAGACG GCCAGTCAAA TTGGCCTGGC  1020
ATGGCGCACT GGTTTCCCGC GAAAAGCACC GCTACTTCGG TACCCTTTGT GACTCACTTT  1080
AATACGGGCA GCGGCGCTCA GTTTTCGGCA GAAGGCAAAA CTGTGTCGGA ACAGGAATGG  1140
AATAACCGCA GCCTTCAAGA TGTGCTGCCG ACATGGCGCT GGATTCAGCA TGGCGGCGAT  1200
TTAGAGGCAA CATTTTCTTG GGAAGAAGCG TTTGAAGGGG GAAGCTCGTT ACAATGGCAT  1260
GGCTCATTAG CGGAAGGAGA ACACGCCCAA ATCGAGCTCT ATCAAACAGA GTTGCCGATA  1320
AGCGAAGGCA CTTCGCTAAC GTGGACATTT AAAAGCGAGC ACGGCAACGA TTTAAATGTG  1380
GGCTTCCGTT TAGATGGGGA AGAGGACTTC CGTTATGTGG AAGGAGAACA GCGTGAATCG  1440
ATAAATGGTT GGACGCAGTG GACGTTGCCG CTGGATGCGT TTGCTGGTCA GACGATAACA  1500
GGGCTGGCAT TTGCAGCGGA AGGGAATGAG ACTGGGCTGG CAGAATTCTA TATTGGACAA  1560
```

```
CTGGCCGTAG GTGCTGATAG CGAAAAGCCT GCCGCTCCAA ACGTGAACGT ACGCCAGTAC    1620

GACCCAGACC CGAGTGGCAT TCAGCTCGTA TGGGAAAAAC AAAGCAACGT CCACCATTAC    1680

CGCGTTTATA AAGAAACAAA GCACGGCAAA GAGCTAATTG GCACATCTGC TGGAGATCGA    1740

ATTTACCTAG AAGGCCTAGT CGAGGAAAGC AAACAAAACG ACGTGCGTCT GCATATAGAA    1800

GCACTAAGTG AAACATTTGT GCCAAGTGAT GCTCGCATGA TCGACATAAA AAGCGGCTCG    1860

TTT                                                                 1863
```

(2) INFORMATION FOR SEQ ID NO:3:

(i) SEQUENCE CHARACTERISTICS:
        (A) LENGTH: 645 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Leu Arg Lys Ala Phe Leu Val Gly Leu Val Cys Thr Ala Cys Val
 1               5                  10                  15

Leu Leu His Asp Asp Pro Val Ala Ala Ser Thr Tyr Asn Gly Pro
                20                  25                  30

Leu Ser Ser His Trp Phe Pro Glu Glu Leu Ala Gln Trp Glu Pro
            35                  40                  45

Asp Ser Asp Pro Asp Ala Pro Phe Asn Arg Ser His Val Pro Leu
        50                  55                  60

Glu Pro Gly Arg Val Ala Asn Arg Val Asn Ala Asn Ala Asp Lys
    65                  70                  75

Asp Ala His Leu Val Ser Leu Ser Ala Leu Asn Arg His Thr Ser
                80                  85                  90

Gly Val Pro Ser Gln Gly Ala Pro Val Phe Tyr Glu Asn Thr Phe
            95                 100                 105

Ser Tyr Trp His Tyr Thr Asp Leu Met Val Tyr Trp Ala Gly Ser
           110                 115                 120

Ala Gly Glu Gly Ile Ile Val Pro Pro Ser Ala Asp Val Ile Asp
           125                 130                 135

Ala Ser His Arg Asn Gly Val Pro Ile Leu Gly Asn Val Phe Phe
           140                 145                 150

Pro Pro Thr Val Tyr Gly Gly Gln Leu Glu Trp Leu Glu Gln Met
           155                 160                 165

Leu Glu Gln Glu Glu Asp Gly Ser Phe Pro Leu Ala Asp Lys Leu
           170                 175                 180

Leu Glu Val Ala Asp Tyr Tyr Gly Phe Asp Gly Trp Phe Ile Asn
           185                 190                 195

Gln Glu Thr Glu Gly Ala Asp Glu Gly Thr Ala Glu Ala Met Gln
           200                 205                 210

Ala Phe Leu Val Tyr Leu Gln Glu Gln Lys Pro Glu Gly Met His
           215                 220                 225

Ile Met Trp Tyr Asp Ser Met Ile Asp Thr Gly Ala Ile Ala Trp
           230                 235                 240

Gln Asn His Leu Thr Asp Arg Asn Lys Met Tyr Leu Gln Asn Gly
           245                 250                 255

Ser Thr Arg Val Ala Asp Ser Met Phe Leu Asn Phe Trp Trp Arg
           260                 265                 270

Asp Gln Arg Gln Ser Asn Glu Leu Ala Gln Ala Leu Gly Arg Ser
```

```
                            275                 280                 285
Pro Tyr Asp Leu Tyr Ala Gly Val Asp Val Glu Ala Arg Gly Thr
                290                 295                 300
Ser Thr Pro Val Gln Trp Glu Gly Leu Phe Pro Glu Gly Glu Lys
                305                 310                 315
Ala His Thr Ser Leu Gly Leu Tyr Arg Pro Asp Trp Ala Phe Gln
                320                 325                 330
Ser Ser Glu Thr Met Glu Ala Phe Tyr Glu Lys Glu Leu Gln Phe
                335                 340                 345
Trp Val Gly Ser Thr Gly Asn Pro Ala Glu Thr Asp Gly Gln Ser
                350                 355                 360
Asn Trp Pro Gly Met Ala His Trp Phe Pro Ala Lys Ser Thr Ala
                365                 370                 375
Thr Ser Val Pro Phe Val Thr His Phe Asn Thr Gly Ser Gly Ala
                380                 385                 390
Gln Phe Ser Ala Glu Gly Lys Thr Val Ser Glu Gln Glu Trp Asn
                395                 400                 405
Asn Arg Ser Leu Gln Asp Val Leu Pro Thr Trp Arg Trp Ile Gln
                410                 415                 420
His Gly Gly Asp Leu Glu Ala Thr Phe Ser Trp Glu Glu Ala Phe
                425                 430                 435
Glu Gly Gly Ser Ser Leu Gln Trp His Gly Ser Leu Ala Glu Gly
                440                 445                 450
Glu His Ala Gln Ile Glu Leu Tyr Gln Thr Glu Leu Pro Ile Ser
                455                 460                 465
Glu Gly Thr Ser Leu Thr Trp Thr Phe Lys Ser Glu His Gly Asn
                470                 475                 480
Asp Leu Asn Val Gly Phe Arg Leu Asp Gly Glu Glu Asp Phe Arg
                485                 490                 495
Tyr Val Glu Gly Glu Gln Arg Glu Ser Ile Asn Gly Trp Thr Gln
                500                 505                 510
Trp Thr Leu Pro Leu Asp Ala Phe Ala Gly Gln Thr Ile Thr Gly
                515                 520                 525
Leu Ala Phe Ala Ala Glu Gly Asn Glu Thr Gly Leu Ala Glu Phe
                530                 535                 540
Tyr Ile Gly Gln Leu Ala Val Gly Ala Asp Ser Glu Lys Pro Ala
                545                 550                 555
Ala Pro Asn Val Asn Val Arg Gln Tyr Asp Pro Asp Pro Ser Gly
                560                 565                 570
Ile Gln Leu Val Trp Glu Lys Gln Ser Asn Val His His Tyr Arg
                575                 580                 585
Val Tyr Lys Glu Thr Lys His Gly Lys Glu Leu Ile Gly Thr Ser
                590                 595                 600
Ala Gly Asp Arg Ile Tyr Leu Glu Gly Leu Val Glu Glu Ser Lys
                605                 610                 615
Gln Asn Asp Val Arg Leu His Ile Glu Ala Leu Ser Glu Thr Phe
                620                 625                 630
Val Pro Ser Asp Ala Arg Met Ile Asp Ile Lys Ser Gly Ser Phe
                635                 640                 645
```

(2) INFORMATION FOR SEQ ID NO:4:

(i) SEQUENCE CHARACTERISTICS:
        (A) LENGTH: 1935 base pairs
        (B) TYPE: nucleic acid (C) STRANDEDNESS: double
        (D) TOPOLOGY: linear (ii) MOLECULE TYPE: genomic DNA (xi) SEQUENCE DESCRIPTION: SEQ ID NO:4:

```
TTGAGAAAAG CTTTTTTAGT CGGTCTTGTT TGCACAGCGT GTGTATTGCT CCATGATGAT      60

CCAGTTGCCG CATCTACGTA CAACGGCCCG CTGTCCTCCC ATTGGTTTCC AGAGGAACTT     120

GCCCAATGGG AACCAGACAG TGATCCAGAC GCACCCTTTA ACAGAAGCCA TGTTCCGCTG     180

GAACCAGGCC GCGTTGCGAA TAGGGTAAAT GCTAATGCAG ACAAGGACGC ACACCTTGTT     240

TCGTTGTCCG CGCTAAACAG GCATACATCA GGTGTTCCAT CGCAAGGAGC GCCAGTTTTC     300

TATGAAAATA CGTTCAGCTA TTGGCATTAT ACAGATTTGA TGGTTTATTG GGCTGGTTCA     360

GCTGGCGAAG GCATTATCGT TCCGCCAAGT GCCGATGTCA TTGATGCATC GCACCGAAAT     420

GGGGTGCCGA TTTTAGGAAA TGTGTTCTTC CCGCCGACGG TTTATGGAGG CAGCTAGAG      480

TGGCTAGAAC AAATGTTAGA GCAAGAGGAG GACGGTTCAT TCCCCCTTGC TGACAAATTG     540

CTAGAAGTCG CAGACTATTA TGGGTTTGAC GGCTGGTTTA TTAACCAAGA AACAGAAGGG     600

GCAGACGAAG GAACAGCCGA AGCCATGCAA GCTTTTCTCG TTTATTTGCA GGAACAAAAG     660

CCAGAAGGCA TGCACATCAT GTGGTATGAC TCGATGATTG ATACAGGGGC GATCGCCTGG     720

CAAAACCATT TAACGGATCG AAATAAAATG TACTTGCAAA ATGGCTCGAC CCGCGTCGCT     780

GACAGCATGT TTTTGAACTT TTGGTGGCGT GACCAGCGCC AATCGAACGA ATTGGCACAA     840

GCACTTGGCA GGTCTCCGTA TGACCTCTAT GCCGGAGTGG ATGTGGAAGC ACGAGGGACA     900

AGTACCCCTG TTCAGTGGGA AGGCCTGTTT CCTGAAGGAG AAAAGGCGCA TACATCACTC     960

GGGTTATACC GTCCAGATTG GCATTTCAG TCAAGTGAAA CAATGGAAGC GTTTTATGAA     1020

AAAGAACTAC AATTTTGGGT TGGCTCGACA GGAAATCCAG CCGAAACAGA CGGCCAGTCA    1080

AATTGGCCTG GCATGGCGCA CTGGTTTCCC GCGAAAAGCA CCGCTACTTC GGTACCCTTT    1140

GTGACTCACT TTAATACGGG CAGCGGCGCT CAGTTTTCGG CAGAAGGCAA AACTGTGTCG    1200

GAACAGGAAT GGAATAACCG CAGCCTTCAA GATGTGCTGC CGACATGGCG CTGGATTCAG    1260

CATGGCGGCG ATTTAGAGGC AACATTTTCT TGGGAAGAAG CGTTTGAAGG GGGAAGCTCG    1320

TTACAATGGC ATGGCTCATT AGCGGAAGGA GAACACGCCC AAATCGAGCT CTATCAAACA    1380

GAGTTGCCGA TAAGCGAAGG CACTTCGCTA ACGTGGACAT TTAAAAGCGA GCACGGCAAC    1440

GATTTAAATG TGGGCTTCCG TTTAGATGGG AAGAGGACT TCCGTTATGT GGAAGGAGAA    1500

CAGCGTGAAT CGATAAATGG TTGGACGCAG TGGACGTTGC CGCTGGATGC GTTTGCTGGT    1560

CAGACGATAA CAGGGCTGGC ATTTGCAGCG GAAGGGAATG AGACTGGGCT GGCAGAATTC    1620

TATATTGGAC AACTGGCCGT AGGTGCTGAT AGCGAAAAGC CTGCCGCTCC AAACGTGAAC    1680

GTACGCCAGT ACGACCCAGA CCCGAGTGGC ATTCAGCTCG TATGGGAAAA ACAAAGCAAC    1740

GTCCACCATT ACCGCGTTTA TAAAGAAACA AAGCACGGCA AGAGCTAAT TGGCACATCT    1800

GCTGGAGATC GAATTTACCT AGAAGGCCTA GTCGAGGAAA GCAAACAAAA CGACGTGCGT    1860

CTGCATATAG AAGCACTAAG TGAAACATTT GTGCCAAGTG ATGCTCGCAT GATCGACATA    1920

AAAAGCGGCT CGTTT                                                     1935
```

(2) INFORMATION FOR SEQ ID NO:5:

(i) SEQUENCE CHARACTERISTICS:
        (A) LENGTH: 22 amino acids
        (B) TYPE: amino acid
        (C) STRANDEDNESS: single (D) TOPOLOGY: linear (ii) MOLECULE TYPE: peptide (v) FRAGMENT TYPE: N-terminal fragment (xi) SEQUENCE DESCRIPTION: SEQ ID NO:5:

Ser Thr Tyr Asn Gly Pro Leu Ser Ser His Xaa Phe Pro Glu Glu
1               5                   10                  15

Leu Ala Gln Xaa Glu Pro Asp
20

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:6:

GTTTGGATCC TTYCCNGARG ARYTNGCNCA                                    30

(2) INFORMATION FOR SEQ ID NO:7:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (v) FRAGMENT TYPE: internal fragment (xi) SEQUENCE DESCRIPTION: SEQ ID NO:7:

Ala Ala His Leu Val Ser Leu Ser Ala Leu Asn Arg His Thr Ser
1               5                   10                  15

Gly Val Pro Ser Gln Gly Ala Pro Val Phe Tyr Glu Asn Thr Phe
20              25                  30

Ser Tyr (2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:8:

GTTTGAATTC ANAGTRTTYT CRTARAANAC                                    30

(2) INFORMATION FOR SEQ ID NO:9:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (v) FRAGMENT TYPE: internal fragment (xi) SEQUENCE DESCRIPTION: SEQ ID NO:9:

```
Ala His Thr Ser Leu Gly Leu Tyr Arg Pro Asp Trp Ala Phe Gln
1               5                   10                  15

Ser Ser Glu Thr Met Glu Ala Phe Tyr Glu Ser Leu
20                  25
```

(2) INFORMATION FOR SEQ ID NO:10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:10:

GTTTGAATTC TCRTARAANG CYTCCATNGT YTC                        33

(2) INFORMATION FOR SEQ ID NO:11:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (v) FRAGMENT TYPE: internal fragment (xi) SEQUENCE DESCRIPTION: SEQ ID NO:11:

```
Ser Thr Ala Thr Ser Val Pro Phe Val Thr His Phe Asn Thr Gly
1               5                   10                  15

Ser Gly Ala Gln Phe Ser Ala Glu Gly Lys
20                  25
```

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO:12:

GTTTGAATTC TGRTTRAART GNGTNACRAA                           30

(2) INFORMATION FOR SEQ ID NO:13:

(i) SEQUENCE CHARACTERISTICS:
        (A) LENGTH: 260 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:13:

GGATCCTTTC CCGGAGAGCT TGCGCAATGG GAACCAGACA GTGATCCAGA CGCACCCTTT    60

AACAGAAGCC ATGTTCCGCT GGAACCAGGC CGCGTTGCGA ATAGGGTAAA TGCTAATGCA   120

GACAAGGACG CACACCTTGT TTCGTTGTCC GCGCTAAACA GGCATACATC ARGTGTTCCA   180

TCGCAAGGAG CGCCAGTTTT CTATGAAAAT ACGTTCAGCT ATTGGCATTA TACAGATTTG   240

```
ATGGTTTATT GGGCTGGTTC                                                      260

(2) INFORMATION FOR SEQ ID NO:14:

(i) SEQUENCE CHARACTERISTICS:
        (A) LENGTH: 359 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:14:

KGTGCGTGGA CCAGCGCCAA TCGAACGAAT TGCACAAGCA CTTTGGCAGG TCTCCGTATG    60

ACCTCTATGC CGGAGTGGAT GTGGAAGCAC GAGGACAAGT ACCCCKGTTC AGTGGAAGGC   120

CTGTTTCCTG AAGGAGAAAA GGCGCATACA TCACTCGGGT TATACCGTCC AGATTGGGCA   180

TTTCAGTCAA GTGAAACAAT GGAAGCGTTT TATGAAAAAG AACTACAATT TGGGGTTGGC   240

TCGACAGGAA ATCCAGCCGA ACAGACGGC CAGTCAAATT GGCCTGGCAT GGCGCACTGG    300

TTTCCCGCGA AAAGCACCGC TACTTCGGTA CCCTTTGTAA CTCACTTTAA CACGAATTC    359

(2) INFORMATION FOR SEQ ID NO:15:

(i) SEQUENCE CHARACTERISTICS:
        (A) LENGTH: 322 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:15:

GCTATTGGCA TTATACMAGA TTTGATGGTT TATTGGGCTG GTTCAGCTGG SCGAAGNCAT    60

TAATCGTTCC GVCCAAGTGC CGATGTCATT GATGCATCGC ACCGAAATGG GGTGCCGATT   120

TTAGGAAATG TGTTCTTCCC GCCGACGGTT TATGGAGGGC AGCTAGAGTG CTAGAACAA    180

ATGTTAGAGC AAGAGGAGGA CGGTTCATTC CCCCTTGCTG ACAAATTGCT AGAAGTCGCA   240

GACTATTATG GGTTTGACGG CTGGTTTATT AACCAAGAAA CAGAAGGGGC AGACGAAGGA   300

ACAGCCGAAG CCATGCAAGC TT                                            322

(2) INFORMATION FOR SEQ ID NO:16:

(i) SEQUENCE CHARACTERISTICS:
        (A) LENGTH: 335 base pairs
        (B) TYPE: nucleic acid
        (C) STRANDEDNESS: double
        (D) TOPOLOGY: linear (ii) MOLECULE TYPE: genomic DNA (xi) SEQUENCE DESCRIPTION: SEQ ID NO:16:

AAGCTTTTCT CGTTTATTTG CAGGAACAAA AGCCAGAAGG CATGCACATC ATGTGGTATG    60

ACTCGATGAT TGATACAGGG GCGATCGCCT GGCAAAACCA TTAACGGAT CGAAATAAAA    120

TGTACTTGCA AAATGGCTCG ACCCGCGTCG CTGACAGCAT GTTTTTGAAC TTTTGGTGGC   180

GTGACCAGCG CCAATCGAAC GAATTGRCAC AARRCACTTG GCAGGTCTCC RTATGACCTC   240

TADTRCCGGA GTAGATGTGG AAGCACGAGG ACAAGTACC CCTGTTCAGT GGGAAGRCCT    300

GTTTCCTGAA GAGAAAGGCG CATACATVAC TCVNG                              335
```